(12) United States Patent
Jameson

(10) Patent No.: US 11,801,072 B2
(45) Date of Patent: *Oct. 31, 2023

(54) MULTI-PORT EPIDURAL NEEDLE

(71) Applicant: Jessica Jameson, Dalton Gardens, ID (US)

(72) Inventor: Jessica Jameson, Dalton Gardens, ID (US)

(*) Notice: Subject to any disclaimer, the term of this patent is extended or adjusted under 35 U.S.C. 154(b) by 122 days.

This patent is subject to a terminal disclaimer.

(21) Appl. No.: 17/511,429

(22) Filed: Oct. 26, 2021

(65) Prior Publication Data

US 2022/0087714 A1  Mar. 24, 2022

Related U.S. Application Data

(63) Continuation of application No. 15/702,111, filed on Sep. 12, 2017, now Pat. No. 11,166,745.

(51) Int. Cl.
*A61B 17/34* (2006.01)
*A61N 1/05* (2006.01)

(52) U.S. Cl.
CPC ...... *A61B 17/3468* (2013.01); *A61B 17/3401* (2013.01); *A61B 17/3496* (2013.01); *A61B 2017/3411* (2013.01); *A61B 2017/3445* (2013.01); *A61N 1/0551* (2013.01)

(58) Field of Classification Search
CPC ............ A61B 17/3468; A61B 17/3469; A61N 1/0551
See application file for complete search history.

(56) References Cited

U.S. PATENT DOCUMENTS

| | | |
|---|---|---|
| 4,808,157 A | 2/1989 | Coombs |
| 4,958,901 A | 9/1990 | Coombs |
| 5,255,691 A | 10/1993 | Otten |
| 5,425,717 A | 6/1995 | Mohiuddin |
| 5,649,959 A | 7/1997 | Hannam et al. |
| 5,733,322 A | 3/1998 | Starkebaum |
| 5,843,048 A | 12/1998 | Gross |
| 5,957,936 A | 9/1999 | Yoon et al. |
| 5,993,466 A | 11/1999 | Yoon |
| 6,309,401 B1 | 10/2001 | Redko et al. |
| 6,554,809 B2 | 4/2003 | Aves |
| 8,112,159 B2 | 2/2012 | Harris et al. |
| 8,287,453 B2 | 10/2012 | Li et al. |
| 9,028,483 B2 | 5/2015 | Long et al. |
| 9,192,759 B2* | 11/2015 | Hamilton ........... A61B 17/1697 |

(Continued)

OTHER PUBLICATIONS

Office Action for U.S. Appl. No. 15/702,111, dated May 5, 2021, Jameson, "Multi-Port Epidural Needle", 10 Pages.

(Continued)

*Primary Examiner* — Phong Son H Dang
(74) *Attorney, Agent, or Firm* — Lee & Hayes, P.C.

(57) ABSTRACT

A needle having a first end, a second end, and a lumen extending within an interior of the needle, between the first end and the second end. A sleeve is engageable within an interior diameter or interior surface of the lumen. The sleeve includes a first end and a second end that are sized to reside within the first end of the lumen and the second end of the lumen, respectively. Ports extend between the first end and the second end of the sleeve. The ports have an inlet and an outlet sized to receive and route stimulator wires to areas within the epidural space of a spine.

20 Claims, 10 Drawing Sheets

(56) References Cited

U.S. PATENT DOCUMENTS

| | | |
|---|---|---|
| 9,220,897 B2 | 12/2015 | Perryman et al. |
| 9,427,570 B2 | 8/2016 | Burdulis |
| 9,510,857 B2 * | 12/2016 | Barker ............... A61N 1/36071 |
| 9,789,314 B2 * | 10/2017 | Perryman ............ A61N 1/0551 |
| 10,213,229 B2 * | 2/2019 | Chitre ................. A61N 1/0551 |
| 10,245,435 B1 | 4/2019 | Perryman et al. |
| 10,448,807 B2 | 10/2019 | Yanuma |
| 10,779,882 B2 * | 9/2020 | Long ...................... A61B 90/08 |
| 2003/0028147 A1 | 2/2003 | Aves et al. |
| 2003/0045919 A1 | 3/2003 | Swoyer et al. |
| 2003/0114905 A1 | 6/2003 | Kuzma |
| 2005/0033393 A1 | 2/2005 | Daglow |
| 2009/0125036 A1 | 5/2009 | Bleich |
| 2009/0222073 A1 | 9/2009 | Flowers et al. |
| 2010/0191267 A1 | 7/2010 | Fox |
| 2011/0098704 A1 | 4/2011 | Long et al. |
| 2011/0202067 A1 | 8/2011 | Falkner et al. |
| 2012/0022454 A1 | 1/2012 | Wall et al. |
| 2012/0253376 A1 | 10/2012 | Liu et al. |
| 2012/0323254 A1 | 12/2012 | Bonde et al. |
| 2014/0018800 A1 | 1/2014 | Yanuma |
| 2014/0039586 A1 | 2/2014 | Barker et al. |
| 2014/0296789 A1 | 10/2014 | El-Mohtar et al. |
| 2015/0073432 A1 | 3/2015 | Barker |
| 2015/0231388 A1 | 8/2015 | Barker |
| 2015/0273208 A1 | 10/2015 | Hamilton |
| 2016/0022118 A1 | 1/2016 | Dejima |
| 2016/0310725 A1 | 10/2016 | De La Rama et al. |
| 2016/0317800 A1 | 11/2016 | Barker |
| 2017/0312500 A1 | 11/2017 | Shoberg et al. |
| 2018/0001062 A1 | 1/2018 | O'Carrol et al. |
| 2018/0042462 A1 | 2/2018 | Yanuma |
| 2019/0076168 A1 | 3/2019 | Jameson |
| 2019/0247660 A1 | 8/2019 | Perryman et al. |
| 2019/0254706 A1 | 8/2019 | Chitre et al. |

OTHER PUBLICATIONS

Office Action for U.S. Appl. No. 15/702,111, dated Oct. 19, 2020, Jameson, "Multi-Port Epidural Needle", 9 PAges.

Non Final Office Action dated Apr. 9, 2020 for U.S. Appl. No. 15/702,111 "Multi-Port Epidural Needle" Jameson, 9 pages.

* cited by examiner

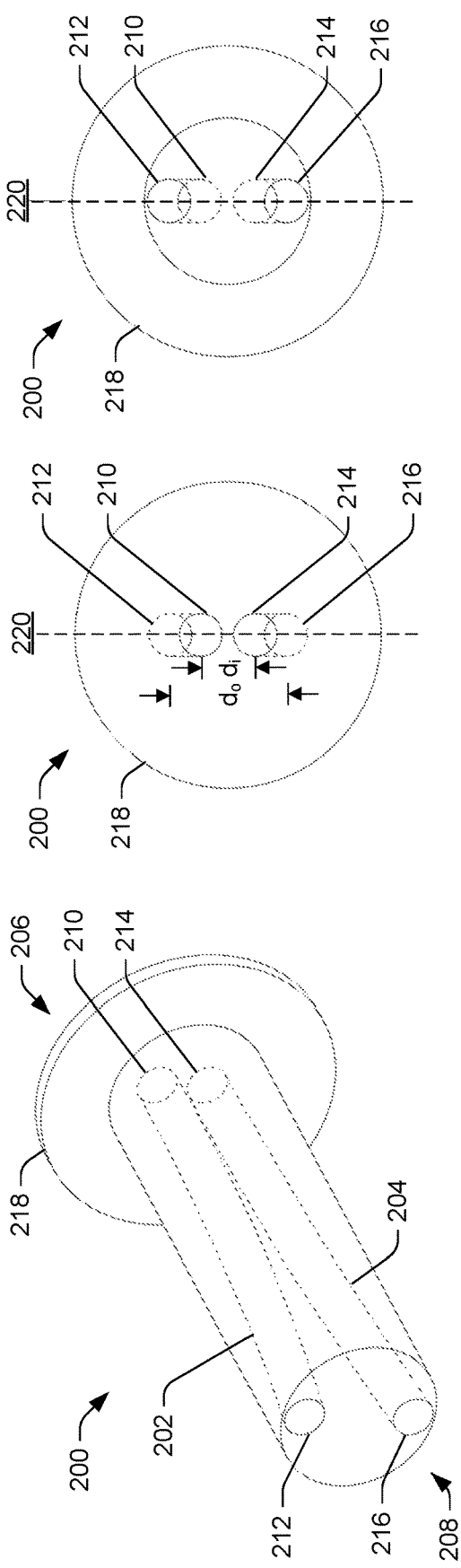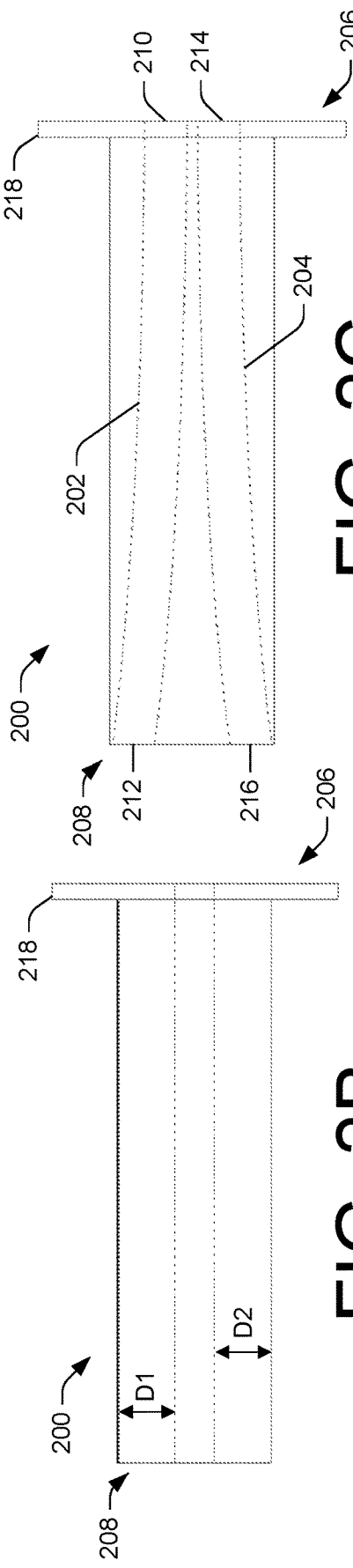

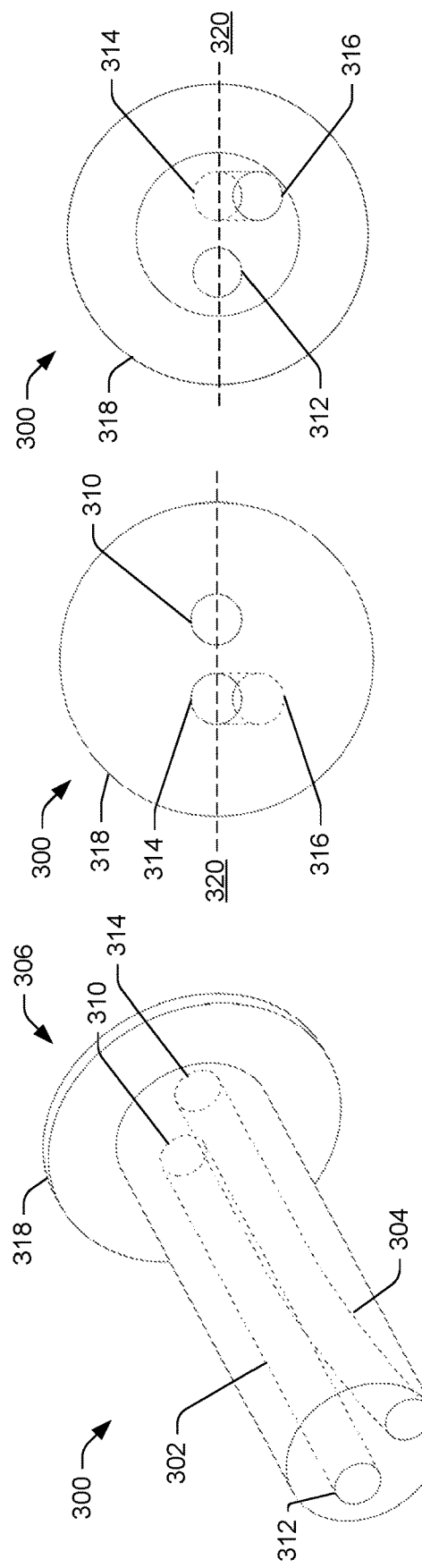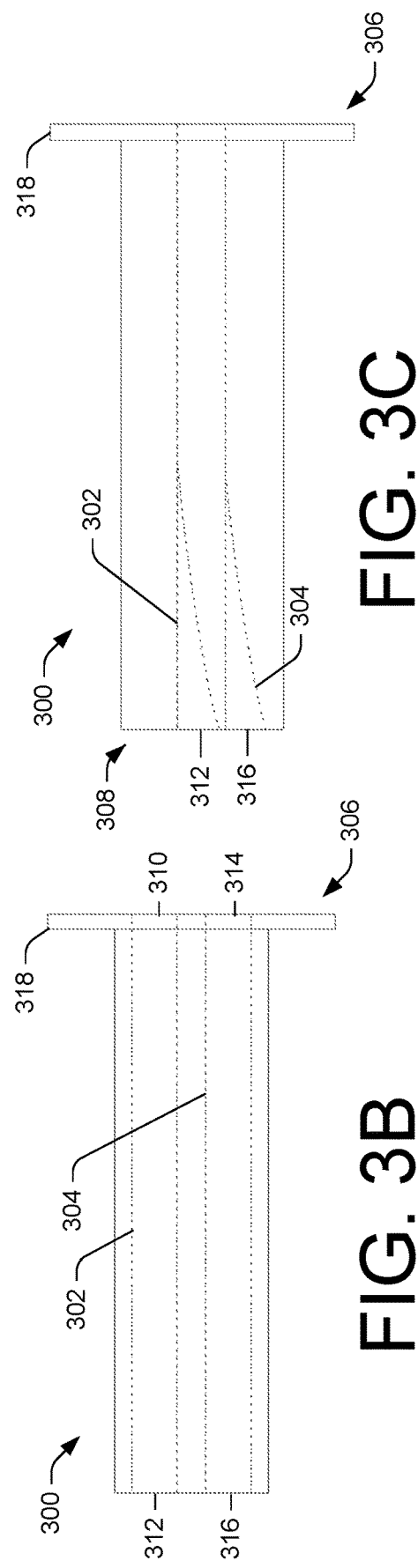

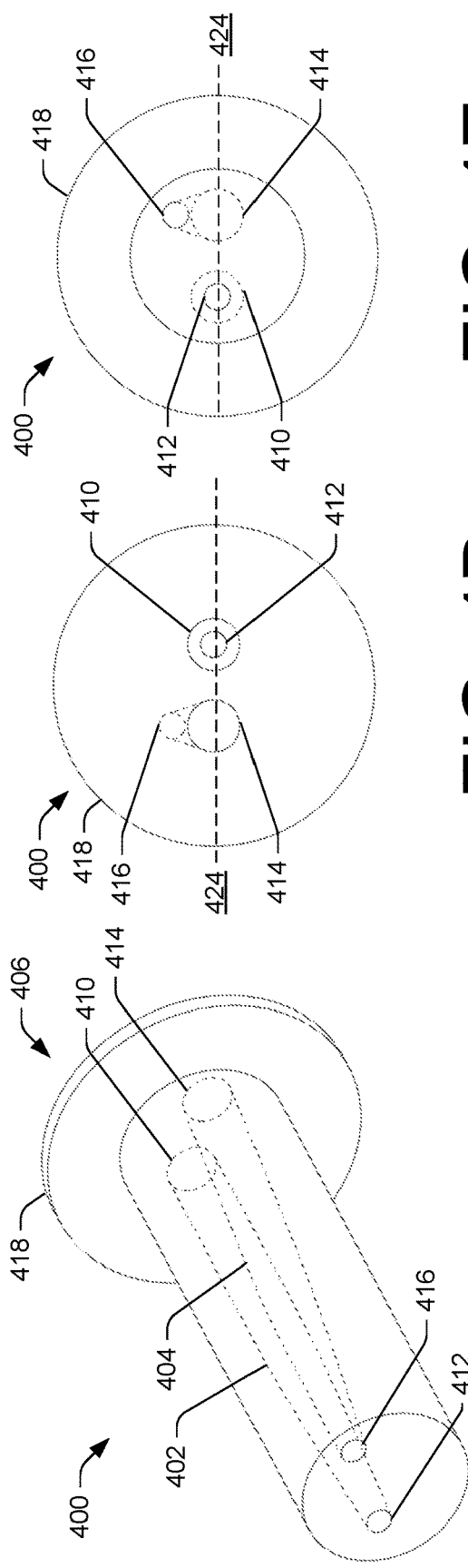
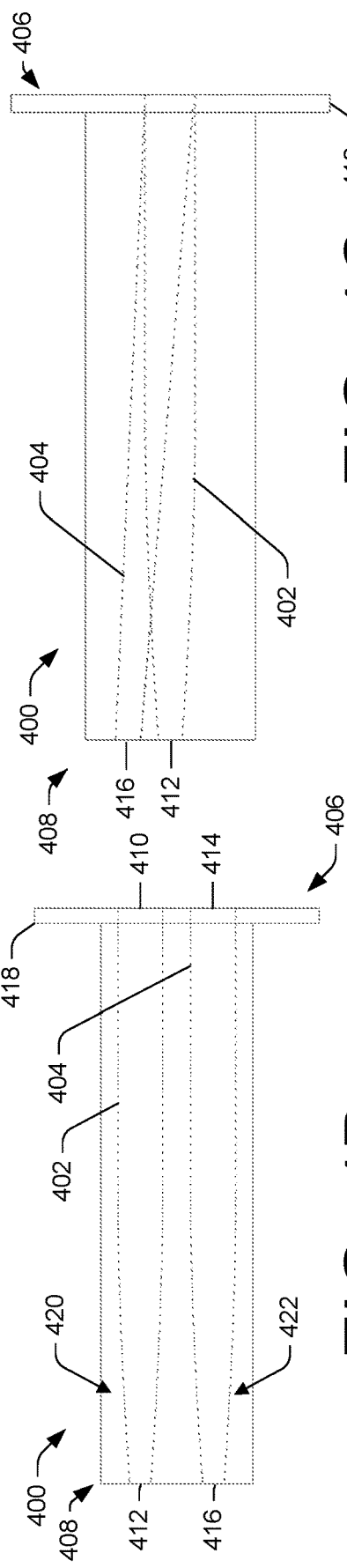

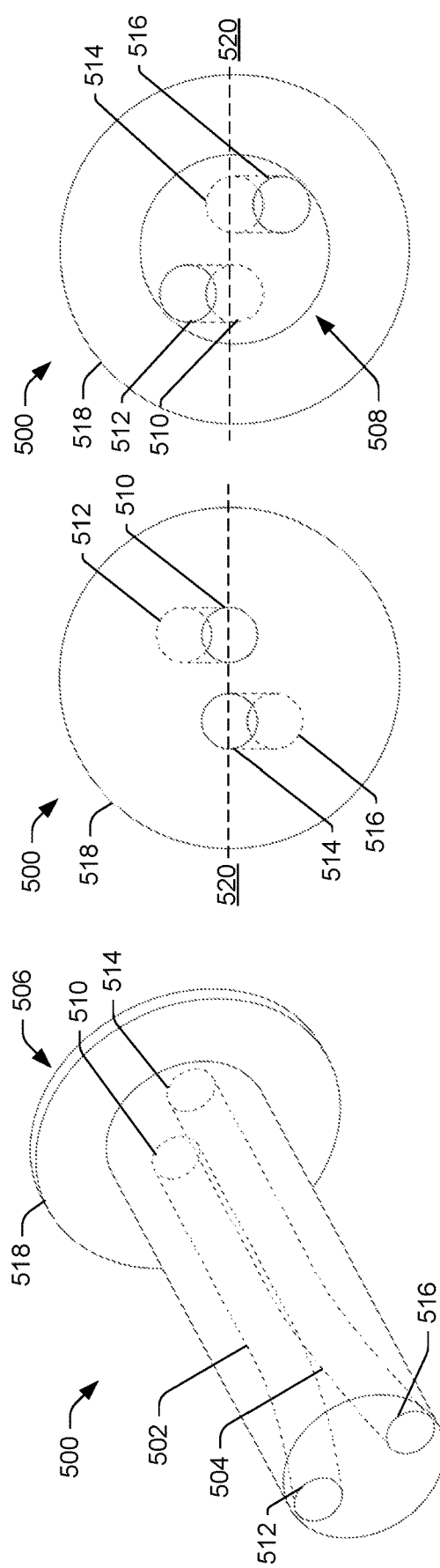
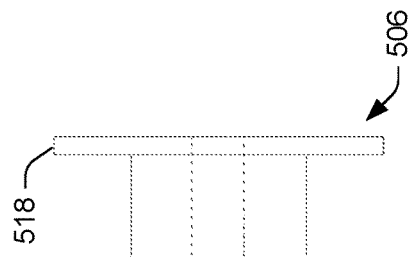
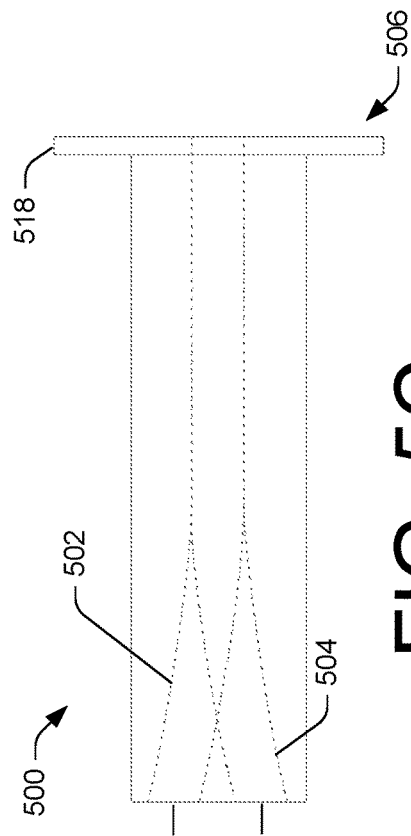
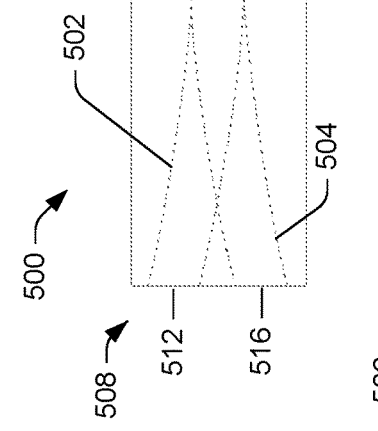
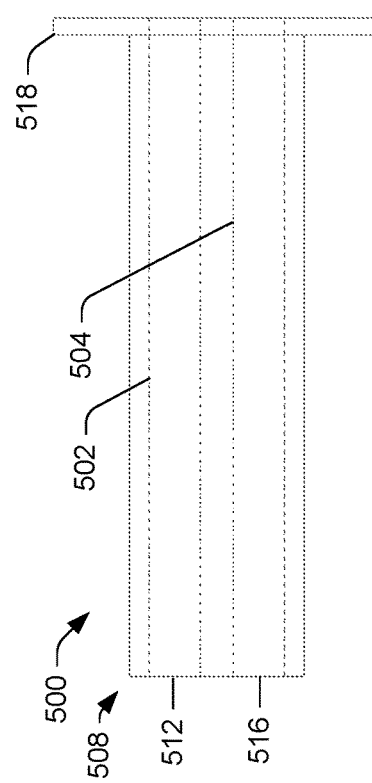

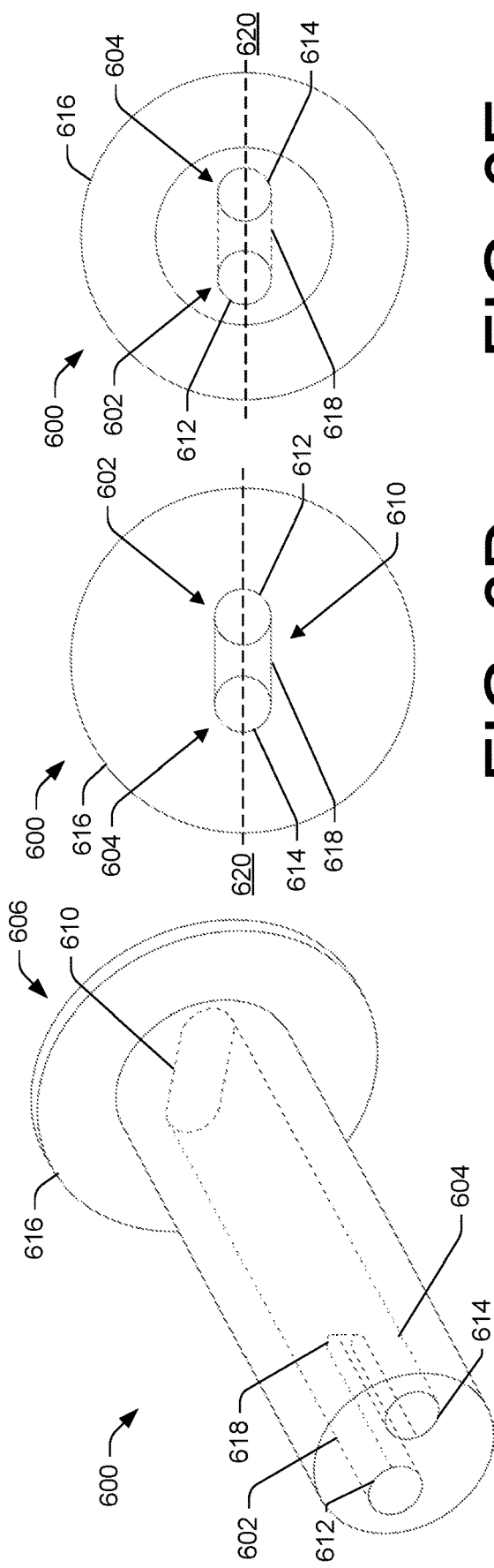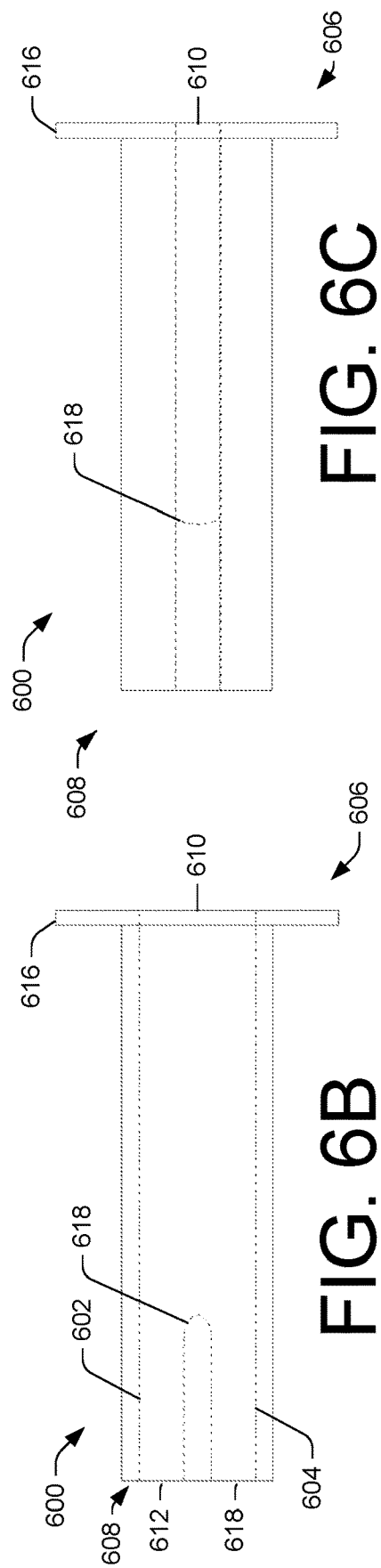

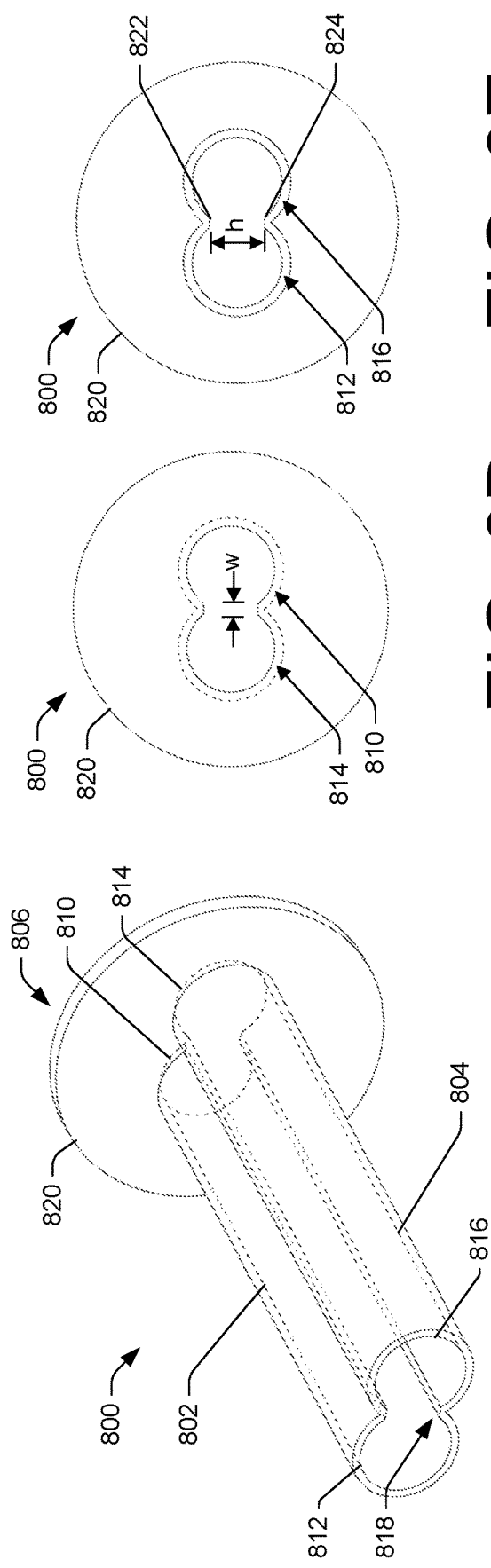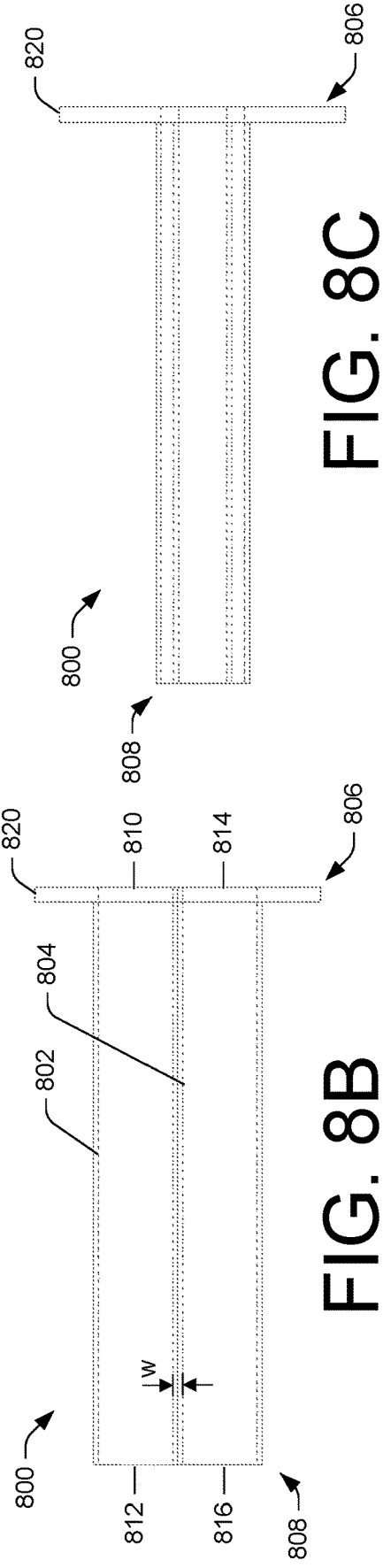

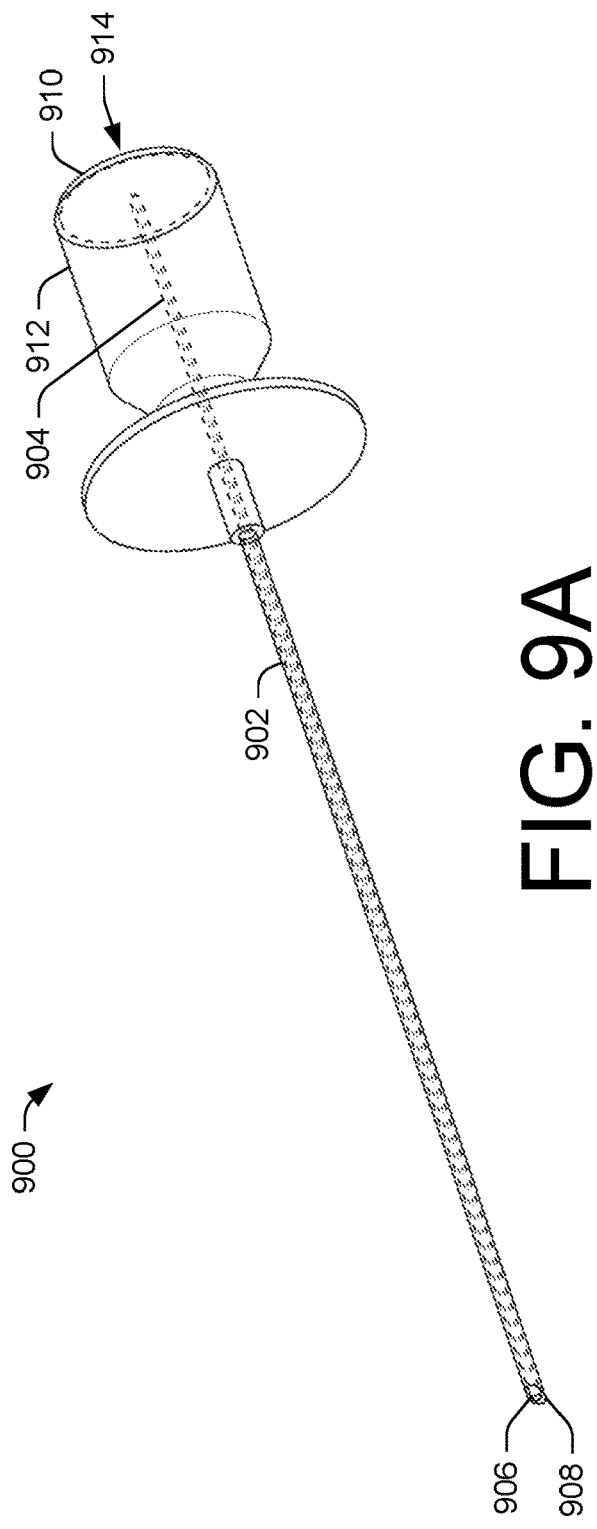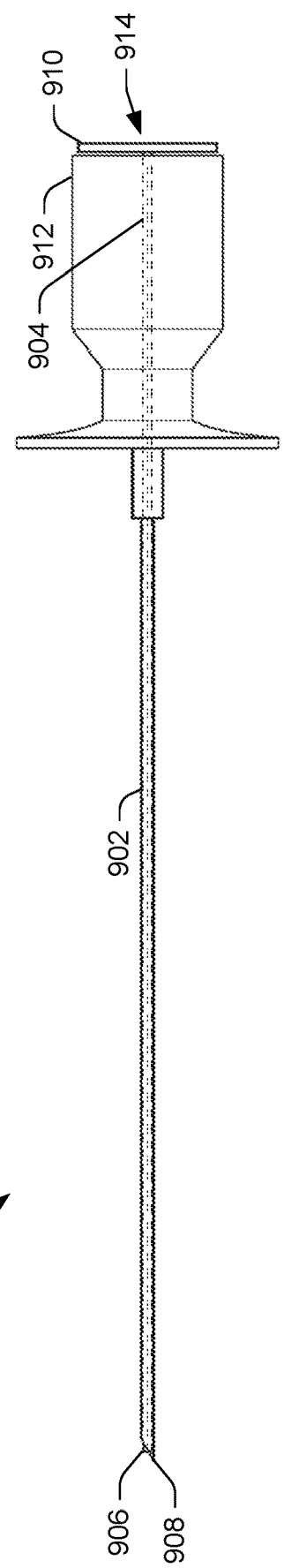
FIG. 9A
FIG. 9B

)# MULTI-PORT EPIDURAL NEEDLE

CROSS-REFERENCE TO RELATED APPLICATION

This patent application claims priority to U.S. patent application Ser. No. 15/702,111, filed Sep. 12, 2017, which is fully incorporated herein by reference.

BACKGROUND

Spinal cord stimulation (SCS), or neurostimulation, is a treatment option that serves to reduce pain and alleviate discomfort by delivering low or mild electrical pulses to the spinal cord. Particularly, SCS attempts to modify, block, or interfere with pain sensations sent to and felt by the brain. Therefore, in operation, a patient undergoing SCS may feel a reduced level of pain and a slight tingling sensation produced by the electrical pulses.

SCS is often performed by implanting stimulator wires under the skin and along the spine within an area called the epidural space. Ends of the stimulator wires have leads that deliver the electrical pulses to the site of pain. To control the electrical pulses, the stimulator wires are connected to a stimulator device. In addition, depending on the pain experienced by a patient, or if a patient is experiencing pain in multiple locations, more than one stimulator wire may be implanted.

While SCS operations are generally safe and the associated treatment is considered effective, surgical operations related to SCS often present risks. One such risk is the possibility of infection when inserting the stimulator wire(s). That is, as alluded to previously, a patient may have multiple insertion sites corresponding to the amount of stimulator wires. However, sterilizing, suturing, and tending to multiple wound sites may increase the risk of infections and associated complications.

BRIEF DESCRIPTION OF THE DRAWINGS

The Detailed Description is set forth with reference to the accompanying figures. In the figures, the left-most digit(s) of a reference number identifies the figure in which the reference number first appears. The use of the same reference numbers in different figures indicates similar or identical items. Furthermore, the drawings may be considered as providing an approximate depiction of the relative sizes of the individual components within individual figures. However, the drawings are not to scale, and the relative sizes of the individual components, both within individual figures and between the different figures, may vary from what is depicted. In particular, some of the figures may depict components as a certain size or shape, while other figures may depict the same components on a larger scale or differently shaped for the sake of clarity.

FIG. 2A illustrates an example embodiment of a sleeve according to the instant application.

FIG. 2B illustrates an example embodiment of a sleeve according to the instant application.

FIG. 2C illustrates an example embodiment of a sleeve according to the instant application.

FIG. 2D illustrates an example embodiment of a sleeve according to the instant application.

FIG. 2E illustrates an example embodiment of a sleeve according to the instant application.

FIG. 3A illustrates an example embodiment of a sleeve according to the instant application.

FIG. 3B illustrates an example embodiment of a sleeve according to the instant application.

FIG. 3C illustrates an example embodiment of a sleeve according to the instant application.

FIG. 3D illustrates an example embodiment of a sleeve according to the instant application.

FIG. 3E illustrates an example embodiment of a sleeve according to the instant application.

FIG. 4A illustrates an example embodiment of a sleeve according to the instant application.

FIG. 4B illustrates an example embodiment of a sleeve according to the instant application.

FIG. 4C illustrates an example embodiment of a sleeve according to the instant application.

FIG. 4D illustrates an example embodiment of a sleeve according to the instant application.

FIG. 4E illustrates an example embodiment of a sleeve according to the instant application.

FIG. 5A illustrates an example embodiment of a sleeve according to the instant application.

FIG. 5B illustrates an example embodiment of a sleeve according to the instant application.

FIG. 5C illustrates an example embodiment of a sleeve according to the instant application.

FIG. 5D illustrates an example embodiment of a sleeve according to the instant application.

FIG. 5E illustrates an example embodiment of a sleeve according to the instant application.

FIG. 6A illustrates an example embodiment of a sleeve according to the instant application.

FIG. 6B illustrates an example embodiment of a sleeve according to the instant application.

FIG. 6C illustrates an example embodiment of a sleeve according to the instant application.

FIG. 6D illustrates an example embodiment of a sleeve according to the instant application.

FIG. 6E illustrates an example embodiment of a sleeve according to the instant application.

FIG. 8A illustrates an example embodiment of a sleeve according to the instant application.

FIG. 8B illustrates an example embodiment of a sleeve according to the instant application.

FIG. 8C illustrates an example embodiment of a sleeve according to the instant application.

FIG. 8D illustrates an example embodiment of a sleeve according to the instant application.

FIG. 8E illustrates an example embodiment of a sleeve according to the instant application.

FIG. 9A illustrates an example multi-port epidural needle according to the instant application, showing a sleeve that is inserted into a needle.

FIG. 9B illustrates an example multi-port epidural needle according to the instant application, showing a sleeve that is inserted into a needle.

DETAILED DESCRIPTION

Overview

Figure 1:
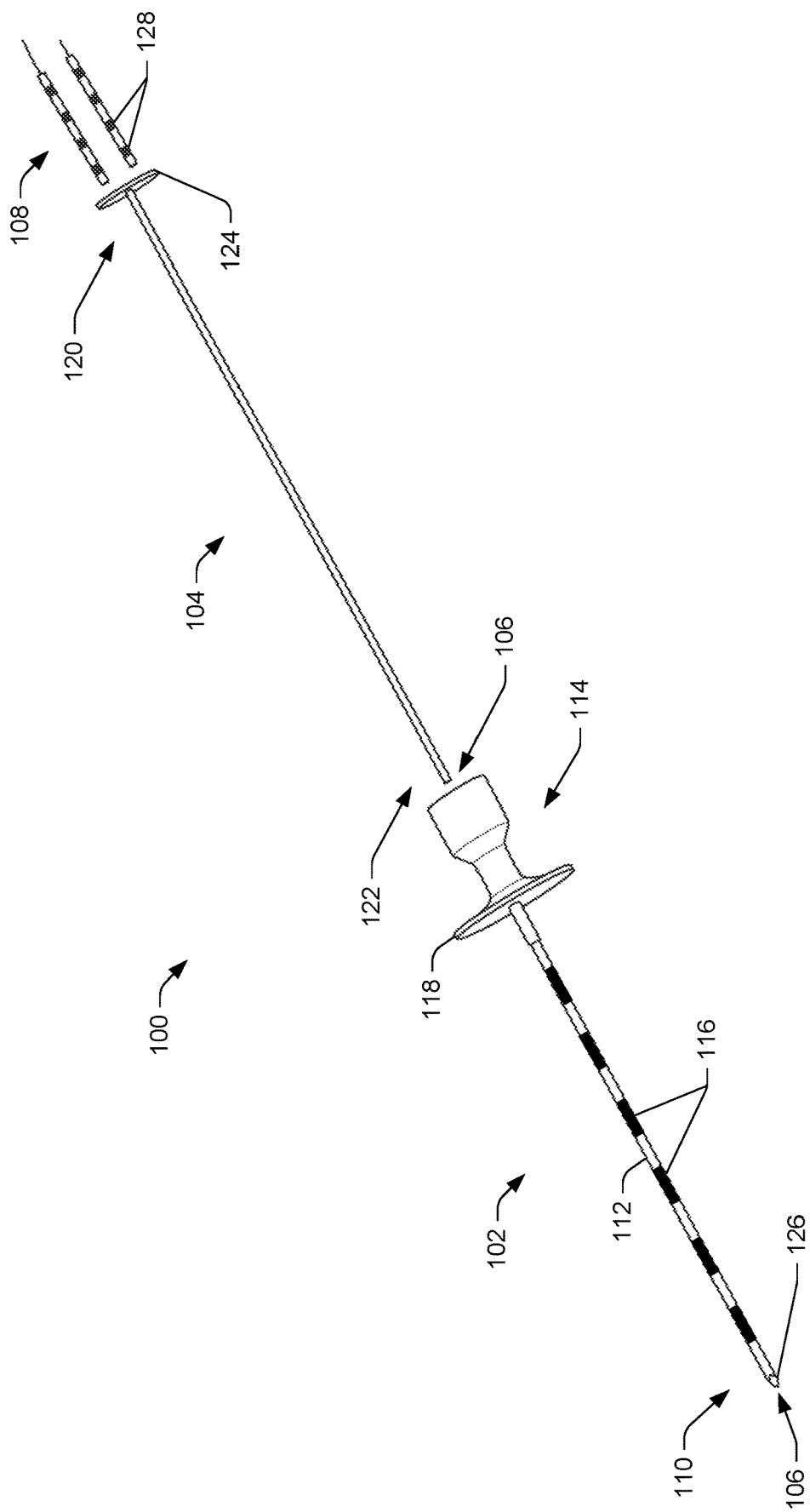
FIG. 1 illustrates a perspective view of an example embodiment of a multi-port epidural needle according to the instant application, showing an epidural needle, a sleeve configured to be inserted into the needle, and stimulator wires sized to insert into the sleeve.

Spinal cord stimulation (SCS) may be used to treat a variety of pain conditions and symptoms, such as those involving nerve damage, by delivering electrical impulses via stimulator wires. The electrical pulses may be generated by a neurostimulator, or other device and delivered to the patient through the stimulator wires. The neurostimulator may be implanted under a patient's skin or may be located external to the patient's skin. The stimulator wires may be thin, flexible, and maneuverable to different places within the epidural space of the spinal cord. As the epidural space contains spinal nerve roots, which are the origin of most of the body's neurological tissues, when the electrical pulses are delivered, SCS stimulates nerves around a pain sight to mask pain signals sent to the brain.

The stimulator wires may have leads or electrodes sites on an end or tip thereof. When implanted, the leads may be positioned adjacent to an area along the spine where a patient's pain exists. For instance, the leads may be placed at T9, T10, T11, and T12 vertebrae, which are located at the base of the spine. That is, the precise location of the lead(s) may depend on the level and/or location of the patient's pain. In addition, while the amount of electrode sites may vary according to the stimulator wire, multiple stimulator wires may also be used in SCS. If the leads of the stimulation wires overlap, or are positioned within the same epidural space, there may exist redundant coverage.

In some instances, SCS may involve using an epidural needle to place the stimulator wires. An epidural needle may include a piercing end, a shaft, and a base end. The piercing end may be sharp so as to puncture or be insertable through a patient's skin and may take a plurality shapes, including, but not limited to being beveled, curved, blunt, conical, or any combination thereof. In some instances, a shape profile of the piercing end may be designed to minimize the chance of inadvertent puncture of the dura mater, a membrane that surrounds the spinal cord.

The shaft of the epidural needle is disposed between the piercing end and the base end. The shaft may be of varying lengths and may contain any number of channel(s), lumens, ports, passageways, keyways, etc., that run down a length thereof. The channels may be used for a plurality of purposes such as to inject medicine, implant catheters, or as discussed in more detail herein, to direct and guide stimulator wires to areas within the epidural space. An outside surface of the shaft may contain markers or other indentations that indicate an insertion distance or depth beneath the patient's skin. More particularly, the markers may help specify the distance the piercing end of the needle is beneath the skin, so as to relay how far the piercing end of the needle is from the epidural space.

The base end of the needle may have handles, flanges, flaps, or other gripping features to facilitate grasping of the needle. The handles may also provide a pushing surface that allows a physician to secure the needle and to increase the pushing force when inserting the needle. The base end may also include an adapter or hub that allows the base end to adjoin with a syringe, for injecting medicine, for instance. That is, the adapter may align the channels within the shaft with an injection port of the syringe.

In some instances, the epidural needle may include a mandrel or stylet equal to the length of the needle shaft. The stylet may occupy a portion of the channel while the needle is being inserted into the patient. The stylet may maintain a stiffness of the needle to help prevent the needle from breaking, twisting, bending, buckling, or otherwise deforming when the needle is inserted into the patient. In addition, an end of the stylet may fill or enclose the piercing end of the needle, making the needle more effective in transmitting or redirecting tissue around the piercing end. After the needle is inserted, the stylet may be removed so as to expose the channel within the interior of the needle. Thereafter, a catheter may be fed through the channel, for instance.

With respect to implanting stimulator leads using an epidural needle, the process may begin by inserting an epidural needle at a desired location on a patient's back or lumbar region. As mentioned above, a lumen of the epidural needle may be occupied by a stylet that provides support against the lumen or epidural needle deforming. Once the patient's ligamentum flavum has been pierced (i.e., lumbar and/or ligament puncture), the stylet may be removed. In some instances, after piercing the lumbar, an end of the epidural needle opposite the piercing end may be connected to a syringe that contains fluid, for instance, saline. Known as the loss-of-resistance technique, an administering physician may apply pressure on a plunger of the syringe so as to press fluid into the epidural needle's lumen. As the needle is advanced further into the patient, once the tip of the needle enters the epidural space, the physician may feel a loss of pressure on the syringe, via expelling fluid out of the needle/syringe. That is, the loss of pressure or loss of resistance felt by pushing on the plunger of the syringe may indicate to the physician that the tip of the needle is within the epidural space. In turn, the syringe may be removed or disconnected from the needle, thereby exposing the lumen(s) within the needle.

A stimulator wire, which is sized smaller than an interior diameter of the lumen, may then be fed into the lumen and out the piercing end or tip end of the needle. Through feeding the stimulator wire down the lumen, the leads may be directed to a particular location within the epidural space. Control or direction of the stimulator wire may be adjusted by moving rotating, panning, or tilting the needle while the stimulator wire is pushed down the needle. Alternatively, and/or additionally, the physician may twist or rotate the stimulator wire to vary the direction. Once positioned, the stimulator wires may be secured using anchors and thereafter, the needle may be retracted while leaving the stimulator wire in place. Next, the exposed end of the stimulator wire may be connected to a neurostimulator or other device to administer the electronic pulses to the lead(s) of the wire.

As mentioned above, multiple stimulator wires may be inserted into the epidural space. Conventionally, stimulator wires are inserted at different locations on a patient. In some instances, this may ensure that the leads are directed to different locations within the epidural space and/or to reduce redundant coverage. That is, when multiple stimulator wires are used, there may exist a corresponding number of insertion sites created by the epidural needles (i.e., each stimulator wire has an associated insertion point). However, the increase in the number of puncture or insertion sites may cause concerns. For instance, increasing the amount of puncture sites may increase the risk of harm to the patient and/or infection both during and after inserting the stimulator wires. In addition, multiple puncture sites may increase the amount of materials needed to prepare, implement leads, and care for the puncture sites. Moreover, while the stimulator wire is being implanted, anesthesia is typically administered to the patient. The use of multiple insertion sites may increase the amount of time the patient is under anesthesia. Furthermore, multiple insertions may lengthen recovery time and may increase the amount of discomfort endured by the patient.

Accordingly, the discussion herein is directed to an epidural needle that may reduce the amount of insertion sites needed to implant stimulator wires. More particularly, an epidural needle according to this disclosure may be used to implant multiple stimulator wires through a single insertion site using the same epidural needle. In general, the epidural needle may be a single lumen needle with a sleeve that is inserted into the lumen. The sleeve may be inserted into the lumen of the needle after the needle has been inserted into the epidural space, for instance, using the loss-of-resistance technique. The sleeve may have multiple ports to route the stimulator wires to different locations within the epidural space, so as to reduce redundant coverage, for instance. In this sense, a single insertion sight may be used for multiple stimulator wires. Therefore, in some instances, the epidural needle may reduce surgery and procedure times, costs, and resources as well as reducing patient recovery time.

Illustrative Embodiment of an Example Multi-Port Epidural Needle

FIG. 1 illustrates an example multi-port epidural needle 100 having a needle 102 and a sleeve 104 that may be inserted into a lumen 106 of the needle 102. The sleeve 104 may include at least two ports that may be used to guide and direct stimulator wires 108 to particular locations within the epidural space of a spine. In some instances, the stimulator wires 108 may be implanted using or integrating the loss-of-resistance technique as described hereinabove. Further, the sleeve 104 may be inserted into the needle 102 after a tip 110 of the needle 102 has been advanced into the epidural space. Therefore, in some instances, using the sleeve 104 with at least two ports, the multi-port epidural needle 102 may be used to implant multiple stimulator wires using a single needle and a single insertion site.

The needle 102 may include the tip 110, or piercing end, that is used to insert the needle 102 through and into the patient's skin. To permit advancing of the needle 102, the tip 110 may be sharp. In addition, while FIG. 1 shows a particular profile or shape of the tip 110, the tip 110 may include other profiles, such as being beveled or curved, for instance.

The needle 102 may include a shaft 112 that spans a distance between the tip 110 and a base end 114 of the needle 102. The shaft 112 may include varying lengths to permit multi-port needle 100 to be used in wide range of applications. The shaft 112 may also include one or more markings 116 (or other indications) relative to the tip 110 of the needle 102. The one or more markings 116 may indicate how far the tip 110 of the needle 102 has been inserted beneath the skin, providing visual feedback regarding how much farther the needle 102 needs to be inserted.

In some instances, a portion of the shaft 112 adjacent or proximate to the tip 110 may be curved. That is, as mentioned above, the portion of the shaft 112 adjacent to the tip 110 may be curved or other flared to prevent inadvertent puncture to the dura mater. However, while FIG. 1 shows a particular embodiment of the shaft 112, in some instances, the tip 100 and/or the shaft 112 or may include differently shaped profiles.

The base end 114 of the needle 102 may include handles 118 (or other grasping points/protrusions) that may assist in securing and holding the needle 102. The handles 118 may be grasped by a physician when the needle 102 is inserted into a patient. The handles 118 may be molded over an exterior surface of the needle 102 proximate to the base end 114 or may be otherwise attached to the base end 114.

The needle 102 may include a lumen 106 that spans or runs a lengthwise direction of the needle 102 between the tip 110 and the base end 114. Ends of the lumen 106 may be exposed through the tip 110 and the base end 114 of the needle 102. With respect to the base end 114, the lumen 106 may extend through the handles 118 or other protrusions located thereon, so as to expose an input of the lumen 106. For instance, while not shown, a stylet having a handle end may be inserted into the lumen 106 such that the handle of the stylet engages or adjoins the handles 118 on the base end 114.

Moving to specifics of the sleeve 104, in an embodiment, the sleeve 104 may generally resemble a cylindrical shape. However, in other alternative embodiments, an exterior profile or surface of the sleeve 104 may be ovular, square, rounded, beveled, or any combination thereof. The sleeve 104 may be sized and configured to be insertable within the lumen 106. To do so, an outer diameter of the sleeve 104 may be sized smaller than an interior diameter of the lumen 106. In instances where the sleeve 104 is not circular, or in other instances, a largest cross-sectional dimension of the sleeve 104 may be smaller than a largest interior dimension of the lumen 106. In addition, when the sleeve 104 is inserted into the lumen 106, only a portion of the sleeve 104 may be in contact with an interior surface of the lumen 106. Furthermore, a length of the sleeve 104 may be shorter, longer, or equal to a length of the needle 102 and/or the lumen 106. The sleeve 104 may also be permitted to rotate within the lumen 106, so as to adjust an orientation of the sleeve 104.

Within the sleeve 104, ports may span the length of the sleeve 104. In some instances, the ports may begin at an input end 120 and end at an output end 122 of the sleeve 104. In a variety of embodiments, along a length of the sleeve 104, the ports may take a plurality of trajectories, respectively, including straight, curved, tapered, bifurcated, or any combination thereof. In some instances, the ports within a single sleeve may be similar or different from one another. That is to say, the ports may take a plurality of shapes, configurations, profiles, cross-sections, and routes as they span along or down the length of the sleeve 104. In addition, the ports may be circular, squared, tapered, hexagonal, or any other shape. In some instances, the output end 122 of the sleeve 104 may contain openings, one for each port, each designed to route and direct a stimulator wire of the stimulator wires 108. The ports may be sized and designed to receive and advance stimulator wires 108 when the stimulator wires are pushed into the ports. In some instances, the sleeve 104 may contain more than two ports.

At the input end 120 of the sleeve 104, a flange 124 (or lip) may be included. The flange 124 may extend outward beyond an exterior surface or largest dimension of the sleeve 104 and may also, in some instances, be sized larger than a diameter or the exterior surface of the needle 102. In some instances, the flange 124 may assist a physician in grasping and sliding the sleeve 104 down into the lumen 106 of the needle 102 and/or removing the sleeve 104 from the needle 102 after the stimulator wires 108 have been inserted. Therefore, the flange 124 may facilitate grasping and retaining a grip thereon. In addition, as mentioned above, given that in some instances there may be a close tolerance between an exterior surface of the shaft 112 and an interior surface of the lumen 106, the flange 124 may assist in providing leverage when removing the sleeve 104 from the needle 102. A bottom surface or edge of the flange 124, when inserted into the lumen 106, may engage or contact an annulus surrounding the base end 114. In some instances, the annulus may be disposed around the base end 114 and adjacent to the handle 118. As such, a bottom surface of the flange 124 may mate, engage, or contact the handle 118. The flange 124 may connect or mate with the annulus of the base end 114 and/or the handle 118 of the needle 102 so as to indicate that the sleeve 104 has been fully inserted within the lumen 106 and that the output end 122 of the sleeve 104 is properly positioned in relation to the tip 110 of the needle 102.

The sleeve 104 may be any length such that when the sleeve 104 is inserted into the lumen 106, the output end 122 is proximate to the tip 110 of the needle 102. The output end 122 of the sleeve 104 may also be offset from a cutting edge 126 of the tip 110, so as to remain residing within the lumen 106 and not be exposed beyond the cutting edge on the tip 110. Alternatively, or in some instances, the output end 122 of the sleeve 104 may protrude or extend beyond the cutting edge 126 of the tip 110, such that when the sleeve 104 is inserted into the lumen 106, the ports are positioned beyond the tip 110.

The tip 110 of the needle 102 may resemble or take a similar profile as that embodied on the output end 122 of the sleeve 104. However, in some instances, the tip 110 of the needle 102 and the output end 122 of the sleeve 104 may embody separate profiles or shapes. For instance, while FIG. 1 shows the output end 122 of the sleeve 104 having a squared-off or planar end, the output end 122 may be rounded, chamfered, cambered, curved, square, or may mirror a profile of the tip 110 or the cutting edge 126.

Once the sleeve 104 is inserted into the lumen 106, the stimulator wires 108 may be directed into the ports of the sleeve 104. For instance, the stimulator wires 108 may be pushed into the ports via a pressing force on a base end of the stimulator wires 108 while holding the handles 118 or the flange 124. Ends of the stimulator wires 108 may include leads or electrode sites 128 that provide electronic pulses to the patient. The leads 128 may take a plurality of appearances, and may resemble paddles, panels, cylinders, etc. The leads 128 may contain row(s) of electrode(s) whose output can be adjusted individually through programming a neurostimulator (not shown). The leads 128 may be of a similar or different size, diameter, or cross-section than the stimulator wires 108. Accordingly, the ports may be sized or configured to receive the largest diameter or cross-sectional dimension of the stimulator wires 108 and/or the leads 128. The stimulator wires 108 may also be of any desired length such that when the leads 128 are positioned within the patient, ends of the stimulator wires opposite to the leads 128 may be exposed external to the patient, so as to permit the exposed ends thereof to be connected to a neurostimulator (not shown).

As mentioned hereinabove, the stimulator wires 108 after being routed through the ports may be directed to different locations within the epidural space of the spine. Stated another way, the pathway and or end points of the ports may diverge and exit at different locations at the output end 122 of the sleeve 104. In some instances, to assist in directing the stimulator wires 108, via the shape or formation of the ports, the ports may be directed or pointed to different locations at the output end 122 of the sleeve 104. Accordingly, when the stimulator wires 108 are passed out the output end 122 of the sleeve 104, they may be directed to different locations within the epidural space. As alluded to previously, to assist in directing the stimulator leads 108, all or a portion of the ports may be straight, tapered, curved inward, curved outward, slanted inward, slanted outward, or any combination thereof. To assist or adjust the direction the stimulator wires 108, as mentioned above, the sleeve 104 may be designed and sized to be rotatable within the lumen 106. Further details regarding the sleeve 104, the ports, and the configuration of the ports along the sleeve 104 are discussed herein below with respect to FIGS. 2-8.

As the stimulator wires 108 are pushed through the sleeve 104, the flange 124 of the sleeve 104 makes contact with the annulus of base end 114 and may prevent the sleeve 104 from falling or otherwise sliding further down into the lumen 106 and out the tip 110 of the needle 102.

After the stimulator wires 108 have been inserted into the patient, the needle 102 and the sleeve 104 may be removed individually or at once. Once removed, ends of the stimulator wires 110 opposite the leads 136 may extrude out of the patient and thereafter, may be connected to the neurostimulator. However, in some instances, after inserting the sleeve 104, the needle 102 may be removed, so as to leave the sleeve 104 within the patient. Thereafter, the stimulator wires 108 may be inserted into the ports, for instance, using the process described above. Thus, the sleeve 104 may be rigid enough hold back tissue and keep the shape of the ports while the stimulator wires 108 are implanted. However, in such instances, the flange 124 on the input end 120 of the sleeve 104 may be removed or be removable, so as to allow the needle 102 to slide over the input end 120 of the sleeve 104.

In some instances, and while not shown, grooves may extend along an interior surface of the ports. The grooves may help in dispelling tissue or fluid, such as skin or blood, as the stimulator wires 108 are inserted into the ports. As such, the stimulator wires 108 may be more easily advanced into the ports as less resistance may be caused by the tissue or blood binding between the stimulator wires 108 and/or leads 128 and an interior surface of the ports. The grooves may be straight, curved, helical, zig-zagged, or a combination thereof and may extend partially or completely down a length of the ports.

In an embodiment, the sleeve 104 may have a minimal thickness and/or sidewalls to thereby minimize the gauge of the needle 102 being used. Thus, the ports may be located closely to each other to minimize the size of needle 102 used.

Inasmuch as multi-port needle 100 is introduced into a patient, the needle 102, the sleeve 104, and stimulator wires 108 may be manufactured and packaged in a sterile setting or may be sterilized before use. Thus, the materials of which the needle 102 and the sleeve 104 may be manufactured include those that may withstand the sterilization process and/or antimicrobial cleansing agents. The materials may include metals, metal alloys, plastics, composites, rubbers, silicone, etc.

Illustrative Embodiments of Sleeves

As discussed above, a sleeve having multiple ports may be engageable or otherwise insertable within a lumen of a needle. In an embodiment, the ports may extend a lengthwise direction of the sleeve and in relation to one another, may diverge from one another along the lengthwise direction. As detailed and illustrated, FIGS. 2-8 show different embodiments of sleeves that may be used in conjunction with an epidural needle. While different configurations, formations, and arrangements are shown with respect to particular embodiments, in some instances, sleeves may include a combination or variation of those sleeves illustrated and discussed with regards to FIGS. 2-8.

Beginning with FIGS. 2A-2E, various views are depicted of a sleeve 200 having a first port 202 and a second port 204 ("ports 202, 204") that extend along a length of the sleeve 200, between an input end 206 and an output end 208 of the sleeve 200.

FIG. 2A illustrates a perspective view of the sleeve 200 showing ports 202, 204 exiting out the output end 208 of the sleeve 200. In some instances, the sleeve 200 may have a cylindrical shape. However, other shapes are also envisioned and a circumference, perimeter, or exterior surface of the sleeve 200 may be sized to reside within a lumen of a needle. The first port 202 may be sized and configured to receive a first stimulator wire and the second port 204 may be sized and configured to receive a second stimulator wire. The first port 202 may have a corresponding inlet 210 and outlet 212. Similarly, the second port 204 may have a corresponding inlet 214 and outlet 216 ("inlets 210, 214" and "outlets 212, 216"). Located around a perimeter or circumference of the input end 206 of the sleeve 200 may be a flange 218. When the sleeve 200 is inserted into the lumen of the needle, the flange 218 may be configured to mate, contact, or otherwise adjoin to an annulus of the lumen. The flange 218 may also provide a grasping point to remove the sleeve 200.

FIG. 2B illustrates a top view of the sleeve 200. As shown, in some instances, the ports 202, 204 may be centered within the sleeve 200 as the ports 202, 204 extend down the length of the sleeve 200. Note that FIG. 2B shows outlines of the first port 202 and the second port 204 overlaying one another. While FIG. 2B shows distances D1, D2 between an exterior surface or sidewall of the ports 202, 204 as being substantially equal in size, in some instances, distances D1, D2 may be different from each other and/or relatively larger or smaller with respect to the outer perimeter of sleeve 200 than is depicted in FIG. 2B. That is, given that the sleeve 200 is inserted into a lumen of a needle, smaller distances D1, D2 may allow for a more compact sleeve, thereby permitting a smaller gauge needle to be used when implanting the stimulator wires. In addition, as mentioned above, smaller distances D1, D2 may allow for the sleeve 200 to more easily rotate with the lumen as less material of the sleeve 200 may be in contact with the inner surface of the lumen of the needle.

FIG. 2C illustrates a side view of sleeve 200 with the ports 202, 204. Shown in FIG. 2C, in some instances, the inlets 210, 214 of the ports 202, 204, may be in close proximity to one another at the input end 206 of the sleeve 200. In some instances, as the ports 202, 204 traverse the length of the sleeve 200, the ports 202, 204 may curve outward towards sidewalls or an exterior surface of the sleeve 200. Stated another way, a distance between a centerline of the first port 202 and a centerline of the second port 204 at the input end 206 of the sleeve 200 may be less than a distance between the centerline of the first port 202 and the centerline of the second port 204 at the output end 208 of the sleeve 200. Accordingly, because the ports 202, 204 diverge from one another at a point after the input end 206, when stimulator wires are inserted into the ports 202, 204, the stimulator wires may exit the sleeve 200 in different or opposite directions. However, while FIG. 2C illustrates the ports 202, 204 curving or being redirected at a certain location along the length of the sleeve 200, the ports 202, 204 may curve at any point along the sleeve 200 so as to exit on the output end 208.

FIGS. 2D and 2E illustrate views of the input end 206 of the sleeve 200 and a view of the output end 208 of the sleeve 200, respectively. FIG. 2D shows that the ports 202, 204 may begin at the input end 206 in relative close proximity to one another. In an embodiment not shown, a center of the inlet 210 of the first port 202 at the input end 206 may be aligned with a center of the inlet 214 of the second port 204 at the input end 206. In some instances, the centers of the inlets 210, 214 may be aligned along a centerline plane 220 of the sleeve 200. As illustrated in FIG. 2E, however, in some instances, the ports 202, 204 may be spaced apart or separated from one another by a greater distance at the output end 208. In some instances, a center of the outlet 212 of the first port 202 at the output end 208 may be aligned with a center of the outlet 216 of the second port 204 along the centerline plane 220. In some instances, the distance between the centers on the input end 206 may be less than a distance between the centers at the output end 208. That is to say, the centers of the inlets 210, 214 of the ports 202, 204 may be separated by a distance $d_i$ at the input end 206 of the sleeve 200. At the output end 208 of the sleeve 200, the centers of the outlets 212, 216 of the ports 202, 204 may be separated by a distance $d_o$ that is greater than $d_i$. Accordingly, as the stimulator wires exit through the output end 208, via ports 202, 204, the stimulator wires may be directed to different locations within the epidural space.

FIGS. 3A-3E illustrate various views of a sleeve 300 having a first port 302 and a second port 304 ("ports 302, 304") that extend down a length of the sleeve 300, between an input end 306 and an output end 308 thereof. The first port 302 may have a corresponding inlet 310 and outlet 312 while similarly, the second port 204 may have a corresponding inlet 314 and outlet 316 ("inlets 310, 314" and "outlets 312, 316"). Located around a perimeter or circumference of the input end 306 may be a flange 318.

FIG. 3A illustrates a perspective view of the sleeve 300 showing ports 302, 304 exiting output end 308 of the sleeve 300. FIG. 3B illustrates a top view of the sleeve 300, showing that, in some instances, the ports 302, 304 may be parallel to one another as they extend down a portion or entire length of the sleeve 300.

FIG. 3C illustrates a side view of the sleeve 300. As shown, in some instances, the first port 302 may extend along an axis between the input end 306 and the output end 308 of the sleeve 300. The second port 302 is shown extending downward as the second port 302 draws from the input end 306 towards the output end 308. Stated another way, centers of the first port 302 and the second port 304 may be aligned on a plane 320 at the input end 306. However, at the output end 308, a center of the first port 302 may be aligned with the plane 320 while a center of the second port 304 is not aligned with the plane 320. In addition, while FIG. 3C shows the second port 304 having a particular slope, the second port 304 may have a trajectory that is more gradual or steeper than that shown.

FIGS. 3D and 3E illustrate views of the input end 306 of the sleeve 300 and a view of the output end 308 of the sleeve 300, respectively. FIG. 3D shows that the ports 302, 304 may begin at the input end 306 in relative close proximity to one another. In some instances, a center of the inlet 310 of the first port 302 at the input end 306 may be aligned with a center of the inlet 314 of the second port 304 at the input end 306. In some instances, the centers of the inlets 310, 314 at the input end 306 may be aligned along a centerline plane 320 of the sleeve 300. As illustrated in FIG. 3E, however, in some instances, the outlets 312, 316 the ports 302, 304 at the output end 308 be spaced apart or separated from one another by a greater distance. In some instances, the first port 302 may extend the length of the sleeve 300 along the plane 320. That is, a center of the outlet 312 of the first port 302 at the output end 308 may be aligned with the plane 320. In some instances, a center of the outlet 316 of the second port 304 at the output end 308 may not be aligned with the plane 320. Stated another way, the second port 304 may diverge from the plane 320 towards an outer perimeter of the sleeve 300 as the second port 304 extends continuously the lengthwise direction of the sleeve 300. Alternatively, and/or additionally, the distance between the centers of the inlets 310, 314 at the input end 306 may be less than a distance between the centers of the outlets 312, 316 at the output end 308. Accordingly, as the stimulator wires exit through the output end 308, the stimulator wires may be directed to different locations within the epidural space.

FIGS. 4A-4E illustrate various views of a sleeve 400 having a first port 402 and a second port 404 ("ports 402, 404") that extend down a length of the sleeve 400, between an input end 406 and an output end 408 of the sleeve 400. The first port 402 may have a corresponding inlet 410 and outlet 412. Similarly, the second port 404 may have a corresponding inlet 414 and outlet 416 ("inlets 410, 414" and "outlets 412, 416"). Located around a perimeter or circumference of the input end 406 may be a flange 418. A circumference, perimeter, or exterior surface of the sleeve 400 may be sized to reside within a lumen of a needle.

FIG. 4A illustrates a perspective view of the sleeve 400 showing ports the 402, 404 extending down the length of the sleeve 400 and exiting out the output end 408 thereof.

FIG. 4B illustrates a top view of the sleeve 400, showing the ports 402, 404 may be parallel to one another as they extend down a portion or entire length of the sleeve 400. FIG. 4B also shows that the ports 402, 404 may include tapered portions 420, 422, respectively. In some instances, the tapered portions 420, 422 may be on a side or interior surface of the ports 402, 404. The tapered portions 420, 422 may be orientated or configured to direct stimulator wires towards an exterior surface of the sleeve 400. Moreover, because the tapered portions 420, 422 are included at the outlet 412 of the first port 402 and the outlet 416 of the second port 404, respectively, the outlets 412, 416 may be smaller than the inlet 410 of the first port 402 and the inlet 414 of the second port 404. As such, the stimulator wires may have more clearance between the sidewalls or interior surface of the ports 402, 404 at the inlets 410, 414 than at the outlets 412, 416. That is, a diameter of the ports 402, 404 at the output end 408 may be less than a diameter of the ports 402, 404 at the input end 406 of the sleeve 400. Moreover, as the leads of the stimulator wires may be inflexible or more rigid that other portions of the stimulator wire, the tapered portions 420, 422 may be gradual so as to permit the leads to be redirected and exit out the outlets 412, 416.

FIG. 4C illustrates a side view of the sleeve 400. As shown, in some instances, the first port 402 may extend along an axis between the input end 406 and the output end 408 of the sleeve 400. The second port 404 is shown extending linearly upward as the second port 402 extends from the input end 406 towards the output end 408. In some instances, a center of the first port 402 and a center of the second port 404 may be aligned along a plane 424 at the input end 406. However, in some instances, at the output end 408, a center of the first port 402 may be aligned with the plane 424 while a center of the second port 404 may not be aligned with the plane 424. In addition, while FIG. 4C shows the second port 404 extending linearly between the input end 406 and the outlet end 408, in some instances the second port 404 may follow a curvilinear trajectory.

FIG. 4D shows that the ports 402, 404 may begin at the input end 406 in relative close proximity to one another. In some instances, a center of the inlet 410 of the first port 402 at the input end 406 may be aligned with a center of the inlet 414 of the second port 404 at the input end 406. In some instances, the centers of the inlets 410, 414 may be aligned along the plane 424. As illustrated in FIG. 4E, however, in an embodiment, the outlets 412, 416 and the ports 402, 404 at the output end 408 be spaced apart or separated from one another by a greater distance than at the input end 406. In some instances, the first port 402 may extend the length of the sleeve 400 along the plane 424. That is, a center of the outlet 412 of the first port 402 may be aligned with the plane 424. In some instances, a center of the outlet 416 of the second port 404 at the output end 408 may not be aligned with the plane 424. Stated another way, the second port 404 may diverge from the plane 424 towards an outer perimeter of the sleeve 400 as the second port 404 extends the lengthwise direction of the sleeve 400. Such illustration is shown in FIG. 4E where the second port 404 diverges from the plane 424. In addition, as noted above, given the configuration of the ports 402, 404, the distance between the centers of the ports 402, 404 at the input end 406 may be less than a distance between the centers of the ports 402, 404 at the output end 408.

FIGS. 5A-5E illustrate various views of a sleeve 500 having a first port 502 and a second port 504 ("ports 502, 504") that extend down a length of the sleeve 500, between an input end 506 and an output end 508 of the sleeve 500. The first port 502 may have a corresponding inlet 510 and outlet 512. Similarly, the second port 504 may have a corresponding inlet 514 and outlet 516 ("inlets 510, 514" and "outlets 512, 516"). Located around a perimeter or circumference of the input end 506 may be a flange 518. A circumference, perimeter, or exterior surface of the sleeve 500 may be sized to reside within a lumen of a needle.

FIG. 5A illustrates a perspective view of the sleeve 500 showing ports the 502, 504 extending down the length of the sleeve 500 and exiting out the output end 508 thereof.

FIG. 5B illustrates a top view of the sleeve 500 with the ports 502, 504. Shown in FIG. 5B, in some instances, the inlets 510, 514 of the ports 502, 504, may be in close proximity to one another at the input end 506 of the sleeve 500 and may be parallel to one another as they extend down a portion or entire length of the sleeve 500.

Shown in FIG. 5C, in some instances, as the ports 502, 504 near the output end 508 of the sleeve 500, the ports 502, 504 may diverge from one another and be directed towards an exterior surface of the sleeve 500. That is, at a point along the length of the sleeve 500, the ports 502, 504 may diverge and exit output end 508 in opposite directions. The ports 502, 504 may flare, curve, or otherwise diverge at similar or different points or locations along the sleeve 500.

FIG. 5D shows that the ports 502, 504 may begin at the input end 506 in relative close proximity to one another. In some instances, a center of the inlet 510 of the first port 502 at the input end 506 may be aligned with a center of the inlet 514 of the second port 504 at the input end 506. In some instances, the centers of the inlets 510, 514 may be aligned along a plane 520 of the sleeve 500. As illustrated in FIG.

5E, however, in some instances, the outlets 512, 516 the ports 502, 504 at the output end 508 may be spaced apart or separated from one another by a greater distance. In some instances, a center of the outlet 512 of the first port 502 may be aligned on the plane 520 or along a same axis as the center of the inlet 510 of the first port 502 at the input end 506. In some instances, a center of the outlet 516 of the second port 504 at the output end 508 may not be aligned with the plane 520 or along a same axis as the center of the inlet 514 of the second port 504 at the input end 506. Stated another way, the ports 502, 504 may diverge from the plane 520 towards an outer perimeter of the sleeve 500 as the ports 502, 504 respectively extend the lengthwise direction of the sleeve 500. Such illustration is shown in FIG. 5E where both the ports 502, 504 at output end 508 of the sleeve 500 are positioned relative to a perimeter of the sleeve 500 as compared to the ports 502, 504 at the input end 506. To further explain, a distance between the center of the first port 502 at the input end 506 and a perimeter of the of sleeve 500 may be greater than a distance between the center of the first port 502 at the output end 508 of the sleeve 500. In addition, a distance between the center of the second port 504 at the input end 506 and a perimeter of the of sleeve 500 may be greater than a distance between the center of the second port 504 at the output end 508.

FIGS. 6A-6E illustrate various views of a sleeve 600 having a first port 602 and a second port 604 ("ports 602, 604") that extend down a length of the sleeve 600, between an input end 606 and an output end 608 of the sleeve 600. The first port 602 and the second port may collectively share a single port inlet 610. However, as the first port 602 and the second port 604 extend down the length of the sleeve 600, the single port inlet 610 may split, forming an outlet 612 of the first port 602 on the output end 608 and an outlet 614 of the second port 604 on the output end 608. In some instances, the single port inlet 610 may resemble an ovular shape or may be circular, square, hexagonal, etc. Located around a perimeter or circumference of the input end 606 may be a flange 616. A circumference, perimeter, or exterior surface of the sleeve 600 may be sized to reside within a lumen of a needle.

FIG. 6A illustrates a perspective view of the sleeve 600 showing ports the 602, 604 extending down the length of the sleeve 600 and exiting out the output end 608 thereof.

FIG. 6B illustrates a top view of the sleeve 600. At the input end 606 of the sleeve 600, the ports 602, 604 may be adjoined or connected to form the single port inlet 610. As the single port inlet 610 extends down the length of the sleeve 600, in some instances the ports 602, 604 may separate from one another, so as form the first port 602 and the second port 604. Separation of the ports 602, 604 may come by way of a split 618 disposed along a centerline of the sleeve 600. However, the split 618 may be disposed along any location or point of the sleeve 600. In some instances, because the split 618 may introduce a taper into the ports 602, 604, when the stimulator wires are inserted, there may be less of a tolerance between sidewalls of the outlet 612, 614 than at the single port inlet 610.

In operation, stimulator wires may be inserted through the single port inlet 610 either simultaneously or at different instances. As the stimulator wires advance into the sleeve 600 through the single port inlet 610, they may be routed or directed to one of the first port 602 or the second port 604 via the split 618. In this manner, when a subsequent stimulator wire is inserted through the single port inlet 610, it may be directed to the other port (the first port 602 or the second port 604) not occupied by the previously inserted stimulator wire. Accordingly, in some instances, the single port inlet 610 at the input end 606 may allow for the stimulator wires to be more easily inserted into the sleeve 600.

In some instances, and while not shown, ribs, struts, or other dividers may extend down the length of the sleeve 600. That is, the rib(s) may span between the single port inlet 610 and the split 618. The ribs may extend from an interior surface at multiple points and may adjoin or be separated from one another. In some instances, the ribs may help direct a first stimulator wire out of the first port 602 and a second stimulator wire out of the second port 604, respectively.

FIG. 6C illustrates a side view of the sleeve 600. In conjunction with FIGS. 6D and 6E, in some instances, a center of the single port inlet 610, a center of the first port 602 at the output end 608 of the sleeve 600, and a center of the second port 604 at the output end 608 of the sleeve 600 may be on a plane 620. Shown in FIG. 6E, the ports 602, 604 extend out of the output end 608 of the sleeve 600, through the inclusion of the split 618, with their respective centers on the plane 620.

FIGS. 7A-7E illustrate various views of a sleeve 700 having a first port 702 and a second port 704 ("ports 702, 704") that extend down a length of the sleeve 700, between an input end 706 and an output end 708 of the sleeve 700. The first port 702 may have a corresponding inlet 710 and outlet 712. Similarly, the second port 704 may have a corresponding inlet 714 and outlet 716 ("inlets 710, 714" and "outlets 712, 716"). Located around a perimeter or circumference of the input end 706 may be a flange 718. A circumference, perimeter, or exterior surface of the sleeve 500 may be sized to reside within a lumen of a needle.

Figure 7E:
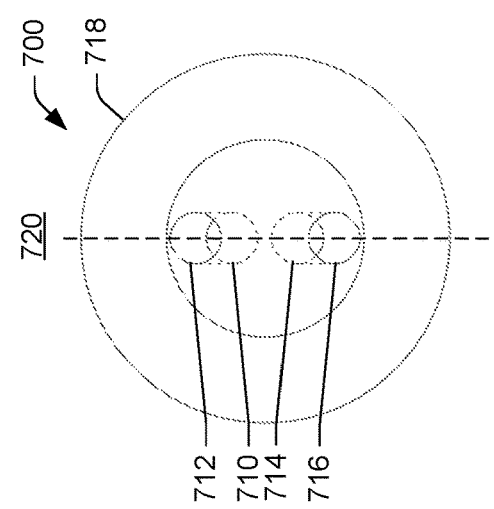
FIG. 7E illustrates an example embodiment of a sleeve according to the instant application.
Figure 7D:
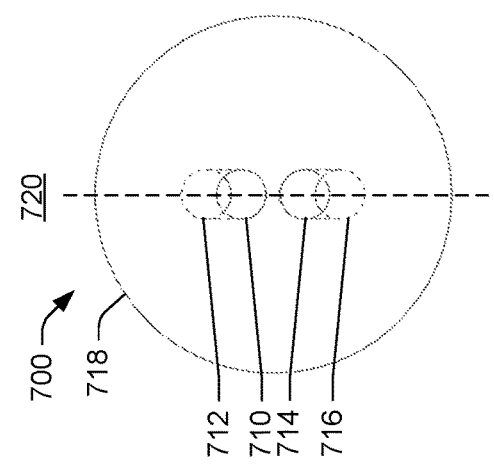
FIG. 7D illustrates an example embodiment of a sleeve according to the instant application.
Figure 7A:
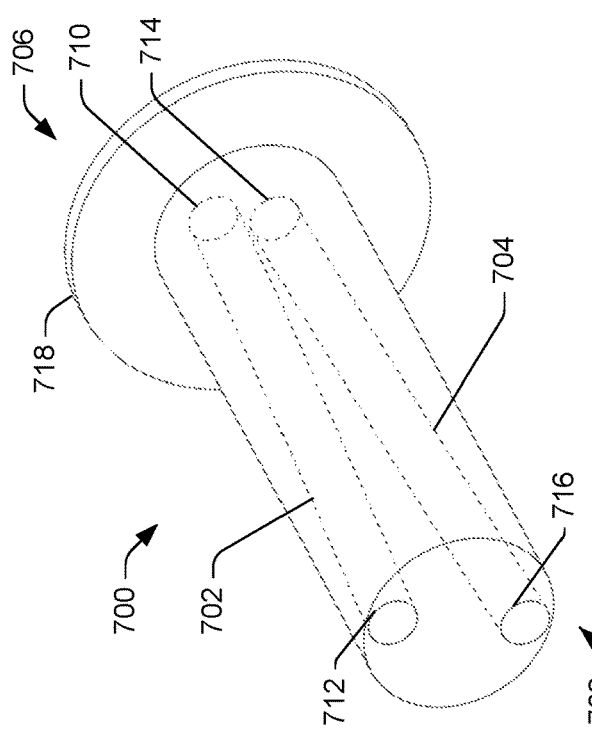
FIG. 7A illustrates an example embodiment of a sleeve according to the instant application.

FIG. 7A illustrates a perspective view of the sleeve 700 showing ports the 702, 704 extending down the length of the sleeve 700 and exiting out the output end 708 thereof.

Figure 7C:
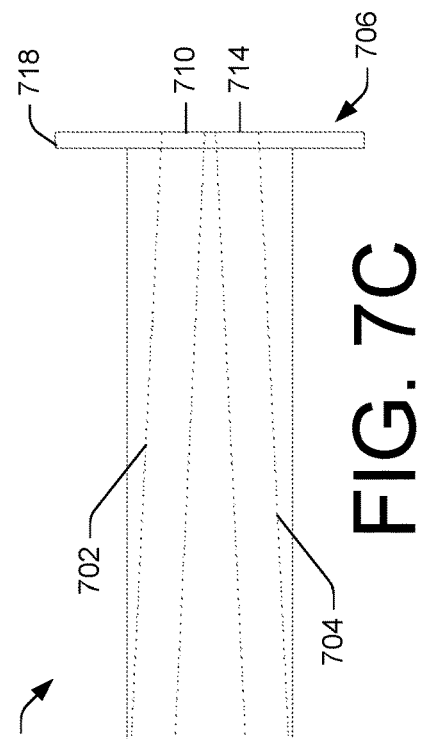
FIG. 7C illustrates an example embodiment of a sleeve according to the instant application.
Figure 7B:
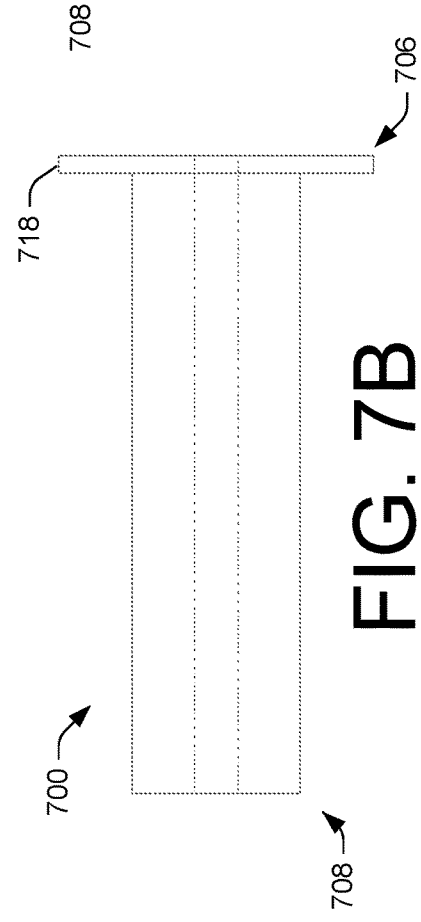
FIG. 7B illustrates an example embodiment of a sleeve according to the instant application.

FIG. 7B illustrates a top view of the sleeve 700, showing that in some instances, the ports 702, 704 may extend down a centerline of the sleeve 700. In some instances, a center of the first port 702 at the input end 706 of the sleeve 700 and a center of the first port 702 at the output end 708 of the sleeve 700 may be on a plane 720. Additionally, or alternatively, in some instances a center of the second port 704 at the output end 708 of the sleeve 700 and a center of the second port 704 at the output end 708 of the sleeve 700 may be on the plane 720.

FIG. 7C illustrates a side view of the sleeve 700. At the input end 706 of the sleeve 700, the ports 702, 704 may be in close proximity to one another. In some instances, the ports 702, 704 may linearly diverge from one another along a lengthwise direction of the sleeve 700 as the ports 702, 704 approach the output end 708. In addition, while the ports 702, 704 are shown diverging from one another at a constant amount, in some instances, the ports 702, 704 may diverge at different angles, rates, or slopes. Moreover, in some instances, the ports 702, 604 may exit the sleeve 700 along an outer perimeter or on the exterior surface of the sleeve 700, rather than at the output end 708. In some instances, the center of the first port 702 at the input end 706 may be spaced farther away from an exterior surface or perimeter of the sleeve 700 than the center of the first port 702 at the output end 708 of the sleeve 700. Similarly, in some instances, the center of the second port 704 at the input end 706 may be spaced farther away from an exterior surface or perimeter of the sleeve 700 than the center of the second port 704 at the output end 708.

FIGS. 7D and 7E illustrate a view of the input end 706 of the sleeve 700 and a view of the output end 708 of the sleeve 700, respectively. With reference to FIG. 7D, at the input end 706, the ports 702, 704 may be adjoined, connected, or in close proximity to one another. In some instances, the inlets 710, 714 may be on the plane 720 at the input end 706. Shown in FIG. 7E, as the ports 702, 704 extend the length of the sleeve 700, the ports 702, 704 may disperse radially outward and deviate or veer from one another, such that centers of the ports 702, 704 at the output end 708 are spaced farther apart from one another than the centers of the ports 702, 704 on the input end 706. That is, in an embodiment, the ports 702, 704 may exit the output end 708 of the sleeve 700 at a farther distance away from one another than at the input end 706 of the sleeve 700.

FIGS. 8A-8E illustrate various views of a sleeve 800 having a first port 802 and a second port 804 ("ports 802, 804") that extend down a length of the sleeve 800, between an input end 806 and an output end 808 of the sleeve 800. The first port 802 may have a corresponding inlet 810 and outlet 812. Similarly, the second port 804 may have a corresponding inlet 814 and outlet 816 ("inlets 810, 812" and "outlets 814, 816"). A channel 818 may span a distance between the ports 802, 804. Located around a perimeter or circumference of the input end 806 may be a flange 820. A circumference, perimeter, or exterior surface of the sleeve 800 may be sized to reside within a lumen of a needle. In some instances, compared to the aforementioned embodiments of a sleeve depicting a cylindrical-shaped structure, the sleeve 800 may have an exterior surface that closely offsets or resembles a shape of the ports 802, 804. That is, in an embodiment, a perimeter or outline of the sleeve 800 may resemble a dumbbell.

FIG. 8A illustrates a perspective view of the sleeve 800 showing ports the 802, 804 extending down the length of the sleeve 800 and exiting out the output end 808 thereof. Interposed between the ports 802, 804 is the channel 818.

FIG. 8B illustrates a top view of the sleeve 800 showing that along a portion or entire length of the sleeve 800 the ports 802, 804 may be parallel to one another. The channel 818 may have a width (w) that spans between the first port 802 and the second port 804. That is, in some instances, the channel 818 may separate the ports 802, 804 along the length of the sleeve 800. In some instances, the channel 818 may adjoin at least a portion of an interior surface of the first port 802 with at least a portion of an interior surface of the second port 804. In some instances, the channel 818 may provide an area for tissue or fluids to occupy as the stimulator leads are advanced through the sleeve 800. In some instances, the channel 818 may be segmented along the length of the sleeve 800, so as to resemble a lattice or latter structure. The segmenting may reduce an amount of sleeve material.

FIG. 8C illustrates a side view of the sleeve 800, showing that in some instances, the ports 802, 804 may extend down a centerline of the sleeve 800. That is, the ports 802, 804 may be centered within the sleeve 800. In some instances, a center of the first port 802 at the input end 806 of the sleeve 800 may be on a same plane as a center of the first port 802 at the output end 808 of the sleeve 800. Additionally, or alternatively, in some instances a center of the second port 804 at the output end 808 of the sleeve 800 may be on a same plane as a center of the second port 804 at the output end 808.

FIGS. 8D and 8E illustrate views of the input end 806 of the sleeve 800 and a view of the output end 808 of the sleeve 800, respectively. As shown, the channel 818 may have a height (h) that is less than a greatest diameter or cross-section of the ports 802, 804. The height (h) of the channel 818 may help retain the stimulator wires within the ports 802, 804 as the stimulator wires are guided into and out of the sleeve 800. Thus, the channel 818 may cut into an interior perimeter of the ports 802, 804, so as to form the raised platforms 822, 824.

Figure 9C:
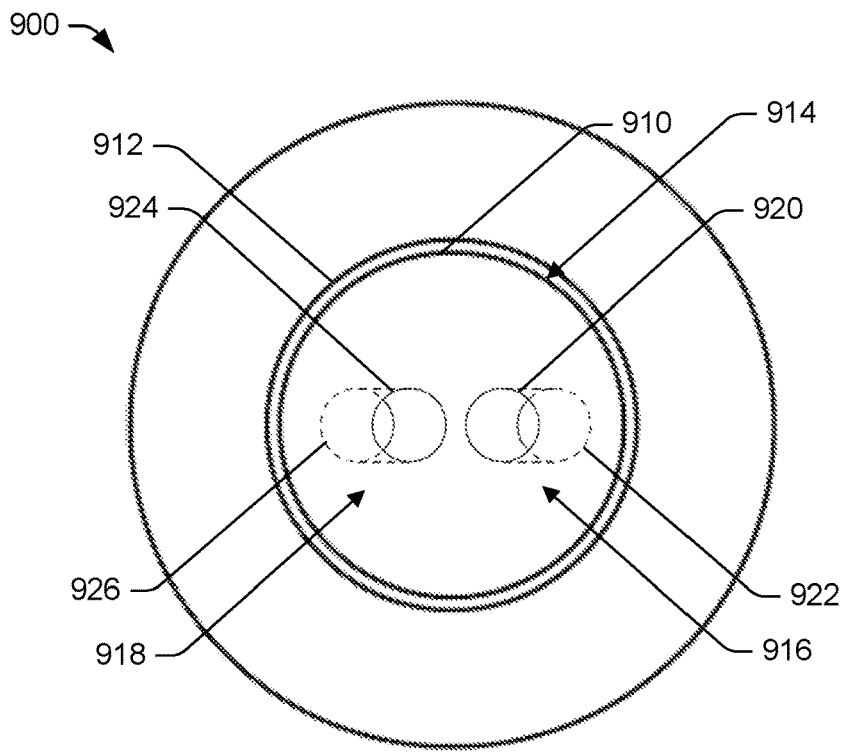
FIG. 9C illustrates an example multi-port epidural needle according to the instant application, showing a sleeve that is inserted into a needle.

FIGS. 9A-9C illustrate various views of an assembled multi-port epidural needle 900. Particularly, FIG. 9A illustrates a perspective view of an assembled multi-port epidural needle 900, FIG. 9B illustrates a side view of the assembled multi-port epidural needle 900, and FIG. 9C illustrates a rear view of the multi-port epidural needle 900. The multi-port epidural needle 900 may include a needle 902 and a sleeve 904 that is inserted into a lumen of the needle 902. A cross-sectional dimension of the sleeve 904 may be sized and configured to be insertable within the lumen of the needle 902. In addition, a length of the sleeve 904 may be sized such that when the sleeve 904 is inserted into the needle 902, an output end 906 of the sleeve 904 resides within, exterior to, or adjacent to a tip 908 of the needle 902. That is, in some instances, the output end 906 of the sleeve 904 may be sized to reside within the tip 908 of the needle 902. As mentioned hereinabove, the output end 906 of the sleeve 904 corresponds to where stimulator leads (not shown) exit the sleeve 904. As such, ports extending down the length of the sleeve 904 may route stimulator wires. The stimulator wires may exit the output end 906 of the sleeve 904 and may extend in opposite directions. The stimulator wires may have leads sized and configured to bend or be redirected based on a configuration of the ports within the sleeve 904. In addition, the sleeve 904 may be rotatable within the lumen of the needle 902 so as to permit the stimulator wires to exit the output end 906 of the sleeve 904 at different orientations, angles, or directions. Moreover, when the sleeve 904 is inserted, a flange 910 on an input end 914 of the sleeve 904 may engage or contact a handle 912 of the needle 902.

While not shown, stimulator wires may enter through the input end 914 of the sleeve 904 and may exit through the output end 906 of the sleeve 904. In some instances, the sleeve 904 may resemble the sleeves discussed and illustrated hereinabove with regards to FIGS. 2-8. As such, the sleeve 904 may have multiple ports that extend a lengthwise direction of the sleeve 900.

FIG. 9C illustrates a rear view of the assembled multi-port epidural needle 900. As shown, the sleeve 904 may include a first port 916 and a second port 918. The first port 916 may include an inlet 920 and an outlet 922. In addition, the second port 904 may include an inlet 924 and an outlet 926. In an embodiment, the input end 914 of the sleeve 904 is sized to reside within an input of a lumen of the needle 902.

Figure 10:
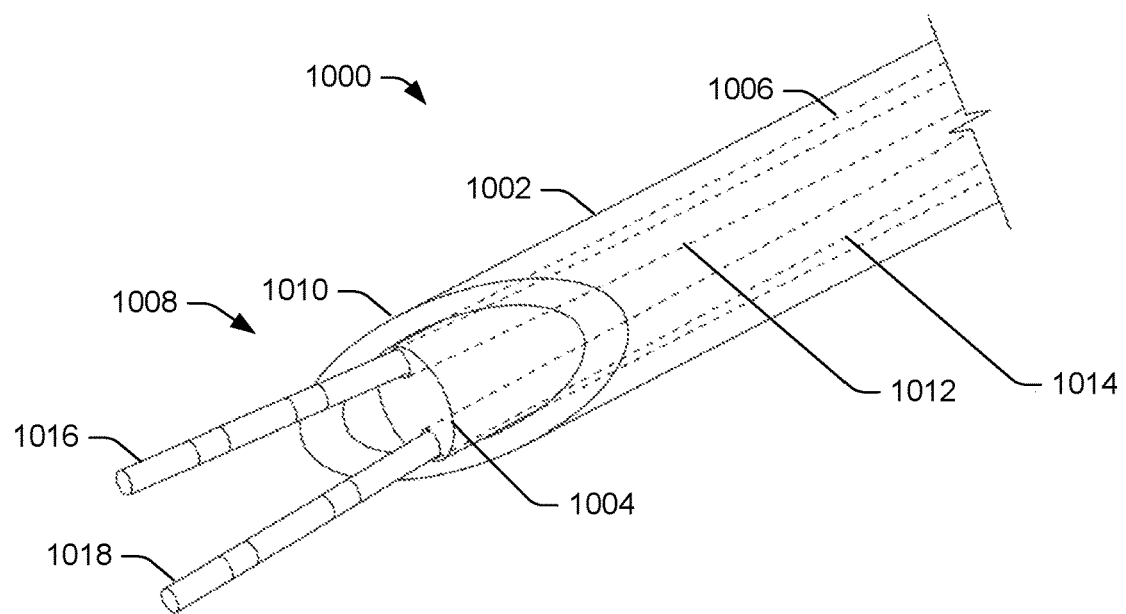
FIG. 10 illustrates a multi-port epidural needle according to the instant application, showing a sleeve that is inserted into a needle and having stimulator wires extending out of the sleeve and a tip end of the needle.

FIG. 10 illustrates a perspective view of an assembled multi-port epidural needle 1000, showing a close-up of a needle 1002 with a sleeve 1004 inserted within a lumen 1006 of the needle 1002. Particularly, FIG. 10 illustrates the sleeve 1004 being exposed out a tip 1008 of the needle 1002. As mentioned previously herein, while FIG. 10 shows the sleeve 1004 exiting at a certain distance relative to a cutting edge 1010 of the needle 1002, in some instances, the sleeve 1004 may be offset from the cutting edge 1010 at different lengths, such as extending out further than as show in FIG. 10 or such as not being exposed at all beyond the cutting edge 1010. In addition, while FIG. 10 shows the sleeve 1004 having a particular cross-section, other cross-sections may also be included, such as being curved, beveled, chamfered, or resembling a profile of the cutting edge 1010 of the needle 1002. Accordingly, the sleeve 1000 may be designed to operate with a plurality of epidural needles having different shapes, tips, or ends.

The sleeve 1004 may include a first port 1012 and a second port 1014 that traverse a length of the sleeve 1004. The first port 1012 and the second port 1014 may be exposed through an output end of the sleeve 1004. As shown, the first port 1012 and the second port 1016 diverge from one another along the length of the sleeve 1004. Accordingly, when a first stimulator wire 1016 is inserted into the first port 1012, the first stimulator wire 1016 may extend in a direction that is different from a second stimulator wire 1018 inserted into the second port 1014. However, while FIG. 10 illustrates a particular embodiment of the sleeve 1004, in some instances, the sleeve 1004 may include different profiles, such as those previously discussed herein. In addition, the first port 1012 and the second port 1014 may also include different trajectories, paths, or profiles, such as those also previously discussed herein.

Alternative Embodiments

While each figure has been shown and discussed as having a certain configuration, in some instances, embodiments from FIGS. 2-9 may be embodied together. For instance, a sleeve may include a tapered port, such as that illustrated in FIG. 4, while also containing a curved port, such as that illustrated in FIG. 5.

In addition, rather than a sleeve being inserted into the lumen and directing multiple stimulator wires, the needle may include features described herein with respect to the sleeve. That is, the needle may include a forked tip that has two ports, for instance.

Conclusion

Although several embodiments have been described in language specific to structural features and/or methodological acts, it is to be understood that the claims are not necessarily limited to the specific features or acts described. Rather, the specific features and acts are disclosed as illustrative forms of implementing the claimed subject matter.

What is claimed is:

1. An apparatus, comprising:
a needle including a first end and a second end opposite the first end, the needle defining a lumen that extends within an interior of the needle between the first end and the second end, the lumen having an interior surface; and
a sleeve engageable with at least a portion of the interior surface of the lumen, the sleeve including:
a proximal end,
a distal end opposite the proximal end, the distal end being sized to fit within the first end of the needle,
a first port extending between the proximal end and the distal end, the first port having a first inlet at the proximal end and a first outlet at the distal end, the first port being configured to receive a first stimulator wire lead, and
a second port extending between the proximal end and the distal end, the second port having a second inlet at the proximal end and a second outlet at the distal end, the second port being configured to receive a second stimulator wire lead.

2. The apparatus of claim 1, wherein the sleeve further includes a flange disposed around at least a portion of a perimeter of the sleeve at the proximal end.

3. The apparatus of claim 1, wherein a first distance between a centerline of the first port and a centerline of the second port at the proximal end is less than a second distance between the centerline of the first port and the centerline of the second port at the distal end.

4. The apparatus of claim 1, wherein the first port and the second port are separate ports within the sleeve.

5. The apparatus of claim 1, wherein the sleeve is substantially cylindrical between the proximal end and the distal end.

6. The apparatus of claim 1, wherein:
the first port curves in a first direction, between the proximal end and the distal end; and
the second port curves in a second direction that is different than the first direction, between the proximal end and the distal end.

7. The apparatus of claim 1, wherein:
the sleeve further includes an exterior surface extending between the proximal end and the distal end; and
at least one of the first port or the second port curves towards the exterior surface along a longitudinal length of the sleeve.

8. The apparatus of claim 1, wherein:
the sleeve is defined by a longitudinal axis; and
a surface at the distal end of the sleeve is substantially perpendicular to the longitudinal axis.

9. A system, comprising:
a needle including a lumen, the lumen having:
a first inlet,
a first outlet, and
an interior surface; and
a sleeve configured to reside within the interior surface of the lumen, the sleeve including:
a first end having a second inlet and a third inlet,
a second end having a second outlet and a third outlet,
a first passage extending between the second inlet and the second outlet, and
a second passage extending between the third inlet and the third outlet.

10. The system of claim 9, wherein the sleeve further includes a flange disposed around at least a portion of the first end, a portion of the flange being engageable with an annulus of the first inlet of the lumen.

11. The system of claim 9, wherein the sleeve comprises a tube-shaped structure having a substantially constant cross-sectional shape.

12. The system of claim 9, wherein the first passage and the second passage are connected along at least a portion of a length of the sleeve.

13. The system of claim 9, wherein:
at the first end of the sleeve, a first distance is disposed between a centerline of the first passage and a centerline of the second passage; and
at the second end of the sleeve, a second distance is disposed between the centerline of the first passage and the centerline of the second passage, the second distance being different than the first distance.

14. The system of claim 9, wherein the first passage and the second passage are sized to receive stimulator wire leads.

15. A needle, comprising:
a first channel including a first inlet, a first outlet, and an interior surface extending between the first inlet and the first outlet; and
a sleeve engageable with at least a portion of the interior surface, between the first inlet and the first outlet, the sleeve including:
a second channel extending in a direction along a length of the sleeve, the second channel having a second inlet and a second outlet, and a third channel extending in the direction along the length of the sleeve, the third channel having a third inlet and a third outlet.

16. The needle of claim 15, wherein the second channel and the third channel are spaced apart along at least a portion of the length of the sleeve.

17. The needle of claim 15, wherein at least a portion of the second channel and the third channel are parallel.

18. The needle of claim 15, wherein at least a portion of at least one of the second channel or the third channel is circular.

19. The needle of claim 15, wherein:
the sleeve includes:
 a first end having the second inlet and the third inlet, and
 a second end having the second outlet and the third outlet; and
at least one of the second channel or the third channel curves towards a sidewall of the sleeve between the first end and the second end.

20. The needle of claim 15, wherein:
the second channel is configured to receive a first lead; and
the third channel is configured to receive a second lead.

* * * * *